United States Patent [19]
Mitchell et al.

[11] Patent Number: 6,022,976
[45] Date of Patent: Feb. 8, 2000

[54] PROCESS FOR THE PRODUCTION OF 5-HYDROXYOXAZOLIDINONES

[75] Inventors: Glynn Mitchell, Cookham; John Michael Cox, Wokingham; Shaheen Khatoon Vohra, Reading, all of United Kingdom

[73] Assignee: ZENECA Limited

[21] Appl. No.: 09/117,489

[22] PCT Filed: Jan. 17, 1997

[86] PCT No.: PCT/GB97/00130

§ 371 Date: Jul. 28, 1998

§ 102(e) Date: Jul. 28, 1998

[87] PCT Pub. No.: WO97/28138

PCT Pub. Date: Aug. 7, 1997

[30] Foreign Application Priority Data

Feb. 2, 1996 [GB] United Kingdom .................. 9602085
Apr. 4, 1996 [GB] United Kingdom .................. 9607212

[51] Int. Cl.$^7$ .................. C07D 263/04; C07D 231/04
[52] U.S. Cl. .................. 548/225; 548/226; 548/110
[58] Field of Search .................. 548/226, 225, 548/110

[56] References Cited

U.S. PATENT DOCUMENTS 5,856,273  1/1999  Kay et al. .................. 504/266

*Primary Examiner*—Johann Richter
*Assistant Examiner*—Dominic Keating
*Attorney, Agent, or Firm*—Marian T. Thomson

[57] ABSTRACT

A process for the production of hydroxy-substituted oxazolidinones, particularly 5-hydroxyoxazolidinones, which are useful as intermediates in the synthesis of herbicidally active compounds, comprising treating a hydroxythiazolidinone with an oxidizing agent.

10 Claims, No Drawings

PROCESS FOR THE PRODUCTION OF 5-HYDROXYOXAZOLIDINONES

The present invention relates to a process for the production of hydroxy-substituted oxazolidinones, particularly 5-hydroxyoxazolidinones which are useful as intermediates in the synthesis of herbicidally active compounds.

Oxazolidinone compounds which are active as herbicides are known from WO 94/13652 and WO 95/33719 (published after the priority date of the present application). These documents disclose inter alia compounds of the formula:

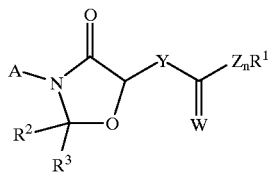

wherein Z is O, S or $NR^4$;

W is O or S;

$R^1$ is hydrogen, or $C_1-C_{10}$ hydrocarbyl or heterocyclyl having 3 to 8 ring atoms either of which may optionally be substituted with halogen, hydroxy, $SO_2NR^aR^b$ (where $R^a$ and $R^b$ independently represent hydrogen or $C_1-C_6$ alkyl), $SiR^c_3$ (where each $R^c$ is independently $C_1-C_4$ alyl or phenyl), cyano, nitro, amino, mono- and di-$C_1-C_6$ alkylamino, acylamino, $C_1-C_6$ alkoxy, $C_1-C_6$ haloalkoxy, $C_1-C_6$ alkylthio, $C_1-C_6$ alkylsufinyl, $C_1-C_6$ alylsulfonyl, carboxy, carboxyamide (in which the groups attached to the N atom may be hydrogen or optionally substituted $C_1-C_{10}$ hydrocarbyl), $C_1-C_6$ alkoxycarbonyl or aryl;

$R^2$, $R^3$ and $R^4$ independently represent hydrogen or $C_1-C_4$ alkyl;

n is 0 or 1;

Y is O, S or $NR^5$;

$R^5$ is hydrogen, hydroxy, CHO or $NR^6R^7$, or $C_1-C_{10}$ hydrocarbyl or $O(C_1-C_{10}$ hydrocarbyl) either of which may be substituted with up to two substituents selected from $OR^6$, $COR^6$, $COOR^6$, $OCOR^6$, cyano, halogen, $S(O)_pR^6$, $NR^6R^7$, nitro, $NR^6COR^7$, $NR^6CONR^7R^8$, $CONR^6R^7$ and heterocyclyl;

$R^6$, $R^7$ and $R^8$ independently represent hydrogen or $C_1-C_6$ hydrocarbyl optionally substituted with one or more halogen atoms;

p is 0, 1 or 2;

alternatively, when Y is $NR^5$ and either Z is $NR^4$ or n is 0, $R^5$ and $R^4$ or $R^1$ may together form a bridge represented by the formula $-Q^1-Q^2-$ or $-Q^1-Q^2-Q^3-$, where $Q^1$, $Q^2$ and $Q^3$ independently represent $CR^9R^{10}$, $=CR^9$, CO, $NR^{11}$, $=N$, O or S;

$R^9$ and $R^{10}$ independently represent hydrogen, $C_1-C_4$ alky, hydroxy or halogen;

$R^{11}$ represents hydrogen or $C_1-C_4$ alkyl;

A is an aromatic or heteroaromatic ring system optionally substituted with one or more substituents selected from halogen, $C_1-C_{10}$ hydrocarbyl, $S(O)_p(C_1-C_{10}$ hydrocarbyl), cyano, nitro, SCN, $SiR^c_3$ (where each $R^c$ is independently $C_1-C_4$ alkyl or phenyl), $COR^{12}$, $CR^{12}NOR^{13}$, NHOH, $ONR^{12}R^{13}$, $SF_5$, $COOR^{12}$, $SO_2NR^{12}R^{13}$, $OR^{14}$ and $NR^{15}R^{16}$; and in which any ring nitrogen atom may be quaternised or oxidised;

alternatively, any two substituents of the group A may combine to form a fused 5- or 6-membered saturated or partially saturated carbocyclic or heterocyclic ring in which any carbon or quaternised nitrogen atom may be substituted with any of the groups mentioned as substituents on A, a ring carbon atom may form part of a carbonyl group or a nitrogen atom may be oxidised;

$R^{12}$ and $R^{13}$ independently represent hydrogen or $C_1-C_{10}$ hydrocarbyl;

$R^{14}$ is hydrogen, $C_1-C_{10}$ hydrocarbyl, $SO_2(C_1-C_{10}$ hydrocarbyl), CHO, $CO(C_1-C_{10}$ hydrocarbyl), COO $(C_1-C_{10}$ hydrocarbyl) or $CONR^{12}R^{13}$;

$R^{15}$ and $R^{16}$ independently represent hydrogen, $C_1-C_{10}$ hydrocarbyl, $O(C_1-C_{10}$ hydrocarbyl), $SO_2(C_1-C_{10}$ hydrocarbyl), CHO, $CO(C_1-C_{10}$ hydrocarbyl), COO $(C_1-C_{10}$ hydrocarbyl) or $CONR^{12}R^{13}$; and any of the hydrocarbyl groups within the group A, whether the hydrocarbyl group is a group on its own or part of a larger group, may optionally be substituted with halogen, hydroxy, $SO_2NR^aR^b$ (where $R^a$ and $R^b$ independently represent hydrogen or $C_1-C_6$ alkyl), cyano, nitro, amino, mono- and di-$C_1-C_6$ alkylamino, acylamino, $C_1-C_6$ alkoxy, $C_1-C_6$ haloalkoxy, $C_1-C_6$ alkylthio, $C_1-C_6$ alkylsulfinyl, $C_1-C_6$alkylsulfonyl, carboxy, carboxyamide (in which the groups attached to the N atom may be hydrogen or $C_1-C_{10}$ hydrocarbyl optionally substituted with halogen), $C_1-C_6$ alkoxycarbonyl or aryl.

Key intermediates in the synthesis of oxazolidinone herbicides such as those mentioned above are hydroxyoxazolidinones of the formula:

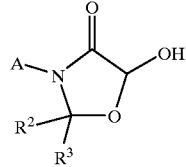

WO 94/13652 discloses general processes for the production of oxazolidinones, for example, introducing an appropriate side chain in a suitable substituted phenyl derivative and cyclising the side chain to form the desired oxazolidinone moiety.

WO 95/33719 discloses processes for the production of hydroxyoxazolidinones comprising:

a) reduction of the corresponding compound of the formula:

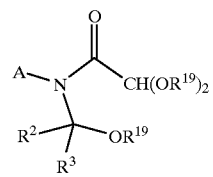

wherein each $R^{19}$ is independently benzyl or substituted benzyl. The reduction is preferably a hydrogenation performed over a palladium or platinum catalyst in the presence of an acid such as trifluoroacetic acid; or b) reaction of the corresponding compound of the formula:

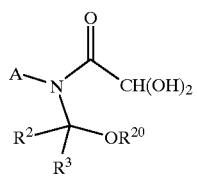

wherein $R^{20}$ is $C_1$–$C_6$ alkyl; with an acid such as hydrochloric acid in an organic solvent such as 1,4-dioxan.

We have now found a novel process for the production of a group of hydroxyoxazolidinones which offers significant advantages over the processes known from the prior art.

According to the invention there is provided a process for the production of a hydroxyoxazolidinone of formula I:

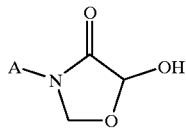

I wherein A is phenyl optionally substituted by one or more substituents selected from halogen, $C_1$–$C_{10}$ hydrocarbyl, $S(O)_p(C_1$–$C_{10}$ hydrocarbyl), cyano, nitro, SCN, $SiR^c_3$ (where each $R^c$ is independently $C_1$–$C_4$ alkyl or phenyl), $COR^{12}$, $CR^{12}NOR^{13}$, $ONR^{12}R^{13}$, $SF_5$, $COOR^{12}$, $S_2NR^{12}R^{13}$, $OR^{14}$ and $NR^{15}R^{16}$;

alternatively, two substituents of the group A may combine to form a fused 5- or 6-membered saturated or partially saturated carbocyclic or heterocyclic ring in which any carbon or quaternised nitrogen atom may be substituted with any of the groups mentioned as substituents on A, a ring carbon atom may form part of a carbonyl group or a nitrogen atom may be oxidised;

p is 0, 1 or 2;

$R^{12}$ and $R^{13}$ independently represent hydrogen or $C_1$–$C_{10}$ hydrocarbyl;

$R^{14}$ is hydrogen, $C_1$–$C_{10}$ hydrocarbyl, $SO_2(C_1$–$C_{10}$ hydrocarbyl), CHO, $CO(C_1$–$C_{10}$ hydrocarbyl), $COO(C_1$–$C_{10}$ hydrocarbyl) or $CONR^{12}R^{13}$;

$R^{15}$ and $R^{16}$ independently represent hydrogen, $C_1$–$C_{10}$ hydrocarbyl, $O(C_1$–$C_{10}$ hydrocarbyl), $SO_2(C_1$–$C_{10}$ hydrocarbyl), CHO, $CO(C_1$–$C_{10}$ hydrocarbyl), $COO(C_1$–$C_{10}$ hydrocarbyl) or $CONR^{12}R^{13}$; and any of the foregoing hydrocarbyl groups, whether the hydrocarbyl group is a group on its own or part of a larger group, may optionally be substituted with halogen, hydroxy, $SO_2NR^aR^b$ (where $R^a$ and $R^b$ independently represent hydrogen or $C_1$–$C_6$ alkyl), cyano, nitro, amino, mono- or di-$C_1$–$C_6$ alkylamino, acylamino, $C_1$–$C_6$ alkoxy, $C_1$–$C_6$ haloalkoxy, $C_1$–$C_6$ alkylthio, $C_1$–$C_6$ alkylsulfinyl, $C_1$–$C_6$ alkylsulfonyl, carboxy, carboxyamide (in which the groups attached to the N atom may be hydrogen or $C_1$–$C_{10}$ hydrocarbyl optionally substituted with halogen), $C_1$–$C_6$ alkoxycarbonyl or aryl;

which process comprises the step of treating a hydroxythiazolidinone of formula II:

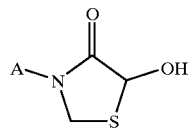

II in which A is as defined for formula I; with an oxidising agent

The expression "$C_1$–$C_{10}$ hydrocarbyl" in the foregoing definitions, whether the expression is used on its own or as part of a larger radical such as, for example, $O(C_1$–$C_{10}$ hydrocarbyl), is intended to include hydrocarbyl radicals of up to ten carbon atoms. Subclasses of such hydrocarbyl radicals include radicals with up to four or up to six carbon atoms. The expression "hydrocarbyl" is intended to include within its scope aliphatic, alicyclic and aromatic hydrocarbyl groups and combinations thereof. It thus includes, for example, alkyl, alkenyl and alkynyl radicals; saturated and unsaturated cycloalkyl radicals e.g. cyclopropyl, cyclopropylmethyl, cyclobutyl, cyclopentyl and cyclohexyl; the adamantyl radical and aromatic radicals e.g. phenyl.

The expression "heterocyclyl" in the foregoing definitions is intended to include both aromatic and non-aromatic radicals containing N, O or S. Examples of aromatic heterocyclyl radicals include pyridyl, pyrimidinyl, triazinyl, thienyl, furyl, oxazolyl, isoxazolyl and thiazolyl, and examples of non-aromatic heterocyclyl radicals include partially and fully saturated variants of the above.

The expression "$C_1$–$C_6$ alkyl" refers to fully saturated straight or branched hydrocarbon chains having from one to six carbon atoms. Examples include methyl, ethyl n-propyl, iso-propyl, t-butyl and n-hexyl. Expressions such as "alkoxy", "cycloalkyl", "alkyithio", "alkylsulfonyl", "alkylsulfinyl" and "haloalkoxy" should be construed accordingly.

The expression "$C_2$–$C_6$ alkenyl" refers to straight or branched hydrocarbon chains having from two to six carbon atoms and at least one carbon-carbon double bond. Examples include ethenyl, 2-propenyl and 2-hexenyl. Expressions such as cycloalkenyl, alkenyloxy and haloalkenyl should be construed accordingly.

The expression "$C_2$–$C_6$ alkynyl" refers to straight or branched hydrocarbon chains having from two to six carbon atoms and at least one carbon-carbon triple bond. Examples include ethynyl 2-propynyl and 2-hexynyl. Expressions such as cycloalkenyl, alkynyloxy and haloalkenyl should be construed accordingly.

Subclasses of the above include alkyl, alkenyl and alkynyl groups with up to 4 or up to 2 carbon atoms.

In the context of the present specification the terms "aryl" and "aromatic ring system" refer to ring systems which may be mono-, bi- or tricyclic. Examples of such rings include phenyl, naphthalenyl, anthracenyl and phenanthrenyl.

In the context of the present specification, the term "heteroaromatic ring system" refers to an aromatic ring system containing at least one heteroatom and consisting either of a single ring or of two or more fused rings. Preferably, single rings will contain up to 4 and bicyclic systems up to 5 heteroatoms which will preferably be chosen from N, O and S. Examples of such groups include furyl, thienyl, pyrrolyl, pyrazolyl, imidazolyl, 1,2,3-triazolyl, 1,2,4-triazolyl, tetrazolyl, oxazolyl, isoxazolyl thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, 1,2,3,4-oxatriazolyl, 1,2,3,5-oxatriazolyl, 1,2,3,4-thiatriazolyl, 1,2, 3,5-thiatriazolyl, pyridyl, pyrimidinyl, pyridazinyl, pyrazinyl, 1,2,3-triazinyl, 1,2,4-triazinyl, 1,3,5-triazinyl, 12,4,5-tetrazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl. Nitrogen atoms in the ring system may be quaternised or oxidised.

In the context of the present specification, the term "fused saturated or partially saturated carbocyclic or heterocyclic ring system" refers to a fused ring system in which a 5- or 6-membered carbocyclic or N, O or S containing heterocyclic ring, which is not of aromatic character, is fused to an aromatic or heteroaromatic ring system. Examples of such ring systems include benzoxazolinyl and benzodioxolyl.

Halogen atoms which the compounds of formula I may be substituted include chlorine, bromine, fluorine and iodine.

The group A preferably represents phenyl optionally substituted with one or more substituents selected from halogen, $C_1$–$C_{10}$ hydrocarbyl and $O(C_1$–$C_{10}$ hydrocarbyl). More preferably A represents phenyl substituted by one or more substituents selected from halogen, $C_1$–$C_4$ alkyl, $C_1$–$C_4$ haloalkyl, $O(C_1$–$C_4$ alkyl) and $O(C_1$–$C_4$ haloalkyl).

The reaction is preferably performed in a solvent comprising a mixture of water and a water-miscible organic solvent, for example, a mixture of water and a lower alkanol. The lower alkanol may be for example methanol or ethanol.

The oxidising agent used in the process may be a periodate salt, e.g. sodium periodate. A preferred oxidising agent comprises a periodate salt, e.g. sodium periodate, together with a catalytic amount of a ruthenium salt. The ruthenium salt is preferably a halide salt and more preferably the trichloride salt The process according to the invention takes place at moderate temperatures, for example, at temperatures in the range 0–100° C. or above, e.g. temperatures in the range of from 20–50° C.

The oxazolidinones of formula I may be isolated by conventional methods, for example by diluting the reaction mixture with water and extracting with a water-immiscible organic solvent, washing the organic extract with an aqueous solution of sodium sulfite to remove any traces of oxidising agent, drying and evaporating the organic extract The residue comprising the crude oxazolidinone may be purified by conventional methods, for example by recrystallisation or chromatography e.g. on silica gel.

The hydroxythiazolidinones of formula II required as starting materials are either known, or may be made by conventional methods, for example as described in WO 94113652.

As mentioned above, compounds of formula I are useful as intermediates in the synthesis of herbicides, therefore, in a further aspect of the invention there is provided a process for the production of a compound of formula III:

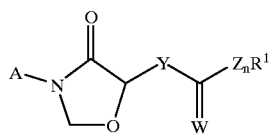

III wherein A is as defined for formula I;
Z is O, S or $NR^4$;
W is O or S;

$R^1$ is hydrogen, or $C_1$–$C_{10}$ hydrocarbyl or heterocyclyl having 3 to 8 ring atoms either of which may optionally be substituted with halogen, hydroxy, $SO_2$ $NR^aR^b$ (where $R^a$ and $R^b$ independently represent hydrogen or $C_1$–$C_6$ alkyl), $SiR^c_3$ (where each $R^c$ is independently $C_1$–$C_4$ alkyl or phenyl), cyano, nitro, amino, mono- and di-$C_1$–$C_6$ alkylamino, acylamino, $C_1$–$C_6$ alkoxy, $C_1$–$C_6$ haloalkoxy, $C_1$–$C_6$ alkylthio, $C_1$–$C_6$ alkylsulfinyl, $C_1$–$C_6$ alkylsulfonyl, carboxy, carboxyamide (in which the groups attached to the N atom may be hydrogen or optionally substituted $C_1$–$C_{10}$ hydrocarbyl), $C_1$–$C_6$ alkoxycarbonyl or aryl;

$R^4$ represents hydrogen or $C_1$–$C_4$ alkyl;

n is 0 or 1;

Y is O, S or $NR^5$;

$R^5$ is hydrogen, hydroxy, CHO or $NR^6R^7$, or $C_1$–$C_{10}$ hydrocarbyl or $O(C_1$–$C_{10}$ hydrocarbyl) either of which may be substituted with up to two substituents selected from $OR^6$, $COR^6$, $COOR^6$, $OCOR^6$, cyano, halogen, $S(O)_pR^6$, $NR^6R^7$, nitro, $NR^6COR^7$, $NR^6CONR^7R^8$, $CONR^6R^7$ and heterocyclyl;

$R^6$, $R^7$ and $R^8$ independently represent hydrogen or $C_1$–$C_6$ hydrocarbyl optionally substituted by one or more halogen atoms;

p is 0, 1 or 2;

alternatively, when Y is $NR^5$ and either Z is $NR^4$ or n is 0, $R^5$ and $R^4$ or $R^1$ may together form a bridge represented by the formula —$Q^1$—$Q^2$— or —$Q^1$—$Q^2Q^3$—, where $Q^1$, $Q^2$ and $Q^3$ independently represent $CR^9R^{10}$, =$CR^9$, CO, $NR^{11}$, =N, O or S;

$R^9$ and $R^{10}$ independently represent hydrogen, $C^1$–$C_4$ alkyl, hydroxy or halogen; and $R^{11}$ represents hydrogen or $C_1$–$C_4$ alkyl;

the process comprising producing a compound of formula I by a process according to the invention and converting it to a compound of formula III by any suitable method.

Examples of methods for converting compounds of formula I to compounds of formula III are described in WO 94/13652 and WO 95/33719 but any method may be used.

For example, a compound of formula I may be converted to a compound of formula III in which Y is O by reaction with a compound of formula $R^1COCl$, $R^1OCOCl$, $R^1$—N=CO=O or $R^1R^4NCOCl$, thus giving rise to compounds of formula m in which W is O and n is 0, Z is O, Z is NH and Z is $NR^4$ respectively. Similarly, a compound of formula I may be converted to a compound of formula m in which Y and Z are both O, by reaction with a compound of formula VI:

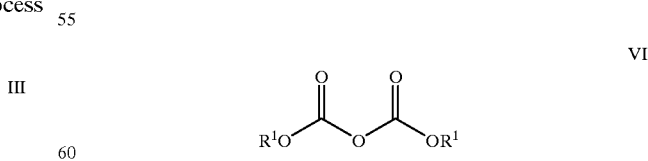

VI

Compounds of formula m in which Y is O, W is S and Z is NH may be prepared by the reaction of a compound of formula I with a compound of formula $R^1$=N=C=S.

Compounds of formula I may be converted into compounds of formula V:

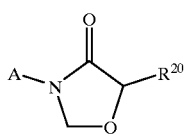

wherein A is as defined for formula I and $R^{20}$ is chloro, methanesulfonyloxy or toluenesulfonyloxy. The compounds in which $R^{20}$ is methanesulfonyloxy or toluenesulfonyloxy may be obtained by reaction with methanesulfonyl chloride or toluenesulfonyl chloride as appropriate although, in some cases, the compound in which $R^{20}$ is chloro may be obtained, particularly in the reaction with methanesulfonyl chloride.

Compounds of formula V may be converted into compounds of formula VI:

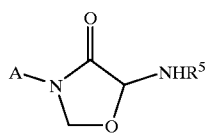

wherein $R^5$ and A are as defined for formula III; by reaction with an alkali metal azide, such as sodium azide, to give the equivalent azide compound followed by reduction of the azide by any known method, for example using a 1,3-propane dithiol in a basic solvent, to give the appropriate compound of formula VI.

Alternatively, a compound of formula V may be reacted with ammonia or an amine of formula $NH_2R^5$.

Compounds of formula VI may be converted to compounds of formula m in which Y is $NR^5$ using the reaction conditions described above for the conversion of compounds of formula I to compounds of formula III.

Compounds of formula V in which $R^{20}$ is halogen may be converted to compounds of formula VII:

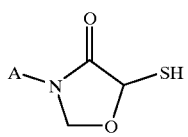

wherein A is as defined for formula I; by reaction firstly with a thioacid of formula VIII:

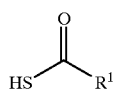

wherein $R^1$ is as defined for formula III; to give a compound of formula III in which Y is S and n is 0; followed by reaction with ammonia in a protic solvent such as methanol. The compound of formula VII may be converted to a compound of formula III using the reaction conditions described above for the conversion of compounds of formula I to compounds of formula III.

Compounds of formula III may also be converted to other compounds of formula III. For example, bridged compounds of formula III in which Y is $NR^5$, Z is $NR^4$, and $R^4$ and $R^5$ form a bridge may be synthesised in a variety of ways which will be apparent to those skilled in the art.

The compounds of formula m are useful as herbicides and show activity against a broad range of weed species including monocotyledonous and dicotyledonous species. They show some selectivity towards certain species, and may be used, for example, as selective herbicides in soya, maize and rice crops. The compounds of formula III may be used on their own to kill or severely damage plants, but are preferably used in the form of a composition comprising a compound of formula III in admixture with a carrier comprising a solid or liquid diluent.

The invention is illustrated by the following Examples. In the examples NMR refers to the proton nuclear magnetic resonance spectrum recorded at 270 MHz in $CDCl_3$ unless otherwise stated.

EXAMPLE 1

3-(3,4-Dichlorophenyl)-5-hydroxyoxazolidin-4-one

A stirred solution of 3-(3,4-dichlorophenyl)-5-hydroxythiazolidin4-one (264 mg, prepared as in Example 1 of WO 94/13652) in methanol (5 ml) was treated with a solution of sodium periodate (852 mg) in water (10 ml). More methanol (5 ml) was added to redissolve the cloudy precipitate which formed. Ruthenium trichioride (10 mg) was added, whereupon the solution turned brown, became warm and a precipitate slowly formed. The resultant slurry was stirred for 2 hours, then water (30 ml) was added and the mixture extracted with ethyl acetate (3×20 ml). The combined ethyl acetate extracts were washed with saturated aqueous sodium sulfite solution (2×20 ml), water (3×20 ml) and brine (20 ml), then dried ($MgSO_4$). Evaporation of the solvent under reduced pressure gave a yellow oil, which was purified by silica-gel chromatography, eluting with ethyl acetate/hexane mixtures, then by high-pressure silica-gel chromatography, eluting with 60% ethyl acetate/hexane, to give the title compound as a white solid (52 mg).

NMR δ: 4.59 (1H,brs), 5.41(1H,d), 5.60 (1H,m), 5.65 (1H,s), 7.35–7.49 (2H,m), 7.72 (1H,d);

MS: m/z 247 ($M^+$)(EI).

EXAMPLE 2

5-Hydroxy-3-(3-trifluoromethoxyphenyl)oxazolidin-4one

Prepared according to the method of Example 1 from the corresponding thiazolidinone prepared as in Example 38 of WO 94/13652.

NMR δ: 5.08 (1H,brs), 5.43 (1H,d), 5.66 (1H,m), 5.69 (1H,s), 7.09 (1H,m), 735–7.45 (2H,m), 7.58 (1H,m).

EXAMPLE 3

3-(3-Bromo-4-chlorophenyl)-5-hydroxyoxazolidin-4-one a) 1-Chloro-2-bromo-4-nitrobenzene Iron (0.35 g) was added to 1chloro-4-nitrobenzene (15.8 g) at 140° C., bromine (2.8 ml) was added dropwise and the mixture heated to 140° C. for 1 hour. Two further additions of iron and bromine were made at 1 hour intervals followed by a final addition of iron (0.07 g) and heating to 140° C. for 1 hour. The reaction mixture was allowed to cool to room temperature, added to sodium metabisulfite solution (200 ml) and stirred for 30 min. The solution was extracted with dichloromethane (×4), washed with aqueous sodium metabisulfite and water then dried (MgSO$_4$) to give an oil which was used in the next step without further purification.

b) 3-Bromo-4-chloroaniline

A mixture of iron (17.9 g), ethanol (120 ml), water (80 ml) and conc. hydrochloric acid (1.5 ml) was heated to 70° C., this temperature was maintained during the addition of 1-chloro-2-bromo-4-nitrobenzene (21.0 g) in ethanol (100 ml) over 25 min. The mixture was heated to reflux for 1¼ hours before adjusting the pH to 9–10 with sodium hydroxide solution. The mixture was filtered hot through Hyflo™ washing with hot ethanol and water. The mixture was concentrated, dichloromethane added and the organic solution washed with water then dried (MgSO$_4$). The product was purifed by silica gel chromatography then recrystalised from ether/hexane to give the sub-title compound as a solid.

NMR δ: 3.70 (2H,s), 6.52–6.58 (1H,m), 6.93–6.95 (1H, d), 7.16–7.20 (1H,d).

c) 3-(3-Bromo-4-chlorophenyl)thiazolidin-4-one

Thioglycolic acid (8.65 g) and 37% aqueous formaldehyde (4.6 ml) was added to a stirred solution of 3-bromo-4-chloroaniline (9.73 g) in toluene (50 ml). The mixture was heated to reflux and the water collected in a Dean and Stark apparatus. After 3 hours the mixture was cooled, diluted with toluene then washed with aqueous sodium hydroxide and water. The organic layer was dried (MgSO$_4$) and concentrated to give the subtitle compound as a solid.

NMR δ: 3.72–3.74 (2H,m), 4.78–4.80 (2H,m), 7.38–7.50 (2H,m), 7.76–7.78 (1H,m).

d) 343-Bromo-4-chlorophenyl)-5-chlorothiazolidin-4-one

Sulfurylchloride (3.83 g) was added over 1 min to a stirred suspension of 3-(3-bromo-4-chlorophenyl) thiazolidin-4-one (7.8 g) in dry dichloromethane (100 ml) at 0° C. The mixture was stirred at 0° C. for 1½ hours then concentrated and the resulting solid triturated with hexane to give the subtitle compound as a solid.

NMR δ: 4.65–4.69 (1H,d), 5.17–5.21 (1H,d), 5.76 (1H,s), 7.40–7.54 (2H,m), 7.82–7.84 (1H,m).

e) 3-3-Bromo-4-chlorophenyl)-5-hydroxythiazolidin-4-one

Dilute hydrochloric acid (50 ml) was added to solution of 3-(3-bromo-4-chlorophenyl)-5-chlorothiazolidin-4-one in THF (50 ml) and stirred at room temperature for 1 hour. The mixture was extracted with ethyl acetate (×2) and the organic extracts washed with water, dried (MgSO$_4$) and concentrated to give the sub-title compound as an orange gum.

NMR δ: 4.63–4.67 (1H,d), 4.97–5.01 (1H,d), 5.70 (1H,s), 7.39–7.50 (2H,m), 7.78–7.80 (1H,d).

f) 3-(3-Bromo-4-chlorophenyl)-5-hydroxyoxazolidin-4-one

Sodium periodate (14.2 g) was dissolved in water (175 ml) and ruthenium trichloride (0.7 g) added to give a black solution. The solution was stirred during the addition of 3-(3-bromo-4-chlorophenyl)-5-hydroxythiazolidin-4-one (7.85 g) in methanol (35 ml) over 5 min, the reaction vessel was cooled in an ice bath to control the resulting exotherm. The mixture was stirred for 1 hour before quenching with sodium metabisulfite. The mixture was extracted with ethyl acetate and the combined organic extracts washed with aqueous sodium metabisulfite solution and water, then dried (MgSO$_4$). Evaporation of the solvent under reduced pressure gave a gum which was triturated with dichloromethane to give the title compound as a grey solid (1.13 g), m.p. 139–140° C.

NMR δ: 5.36–5.38 (1H,d), 5.50–5.60 (2H,m), 6.85–6.89 (1H,d), 7.44–7.54 (2H,m), 7.89–7.91 (1H,m).

EXAMPLE 4

The following compounds were prepared according to the relevant parts of the method of Example 3:

a) 3-(3-Difluoromethoxyphenyl)-5-hdroxyoxazolidin-4-one

NMR δ: 4.90 (1H,brs), 5.44 (1H,d), 5.62–5.67 (2H,m), 6.54 (1H,t), 7.00 (1H,dd), 7.29 (1H,m), 7.39 (1H,t), 7.49 (1H,m).

b) 3-(3-Bromo-4-fluorophenyl)-5-hydroxyoxazolidin-4-one

NMR δ: 5.00 (1H,brs), 5.40–5.42 (1H,d), 5.59–5.63 (1H, m), 5.66 (1H,s), 7.12–7.18 (1H,t), 7.42–7.50 (1H,m), 7.78–7.82 (1H,m).

c) 3-(3,5-Dichloro-4-fluorophenyl)-5-hydroxyoxazolidin-4-one

NMR δ: 4.75 (1H,brs), 5.49–5.51 (1H,d), 5.58–5.66 (2H, m), 7.56–7.60 (2H,d).

d) 3-(3-Chlorolphenyl)-5-hydroxyoxazolidin-4-one

NMR δ: 4.50 (1H,brs), 5.40 (1H,d), 5.60 (2H,m), 7.20–7.40 (3H,m), 7.60 (1H,t).

Thiazolidinone starting material prepared as in Example 5 of WO 94/13652.

e) 3-(3,5-Dichlorophenyl)-5-hydroxyoxazolidin-4-one

NMR δ: 4.30 (1H,brs), 5.40 (1H,d), 5.60 (1H,d), 5.65 (1H,s), 7.20 (1H,t), 7.50 (2H,d).

Thiazolidinone starting material prepared as in Example 6 of WO 94/13652.

f) 3-(3-Chloro-4-fluorophenyl)-5-hydroxyoxazolidin-4-one

NMR δ: 4.85 (1H,brs), 5.40 (1H,d), 5.60 (1H,d), 5.65 (1H,s), 7.15 (1H,t), 7.40 (1H,dt), 7.70 (1H,dd).

Thiazolidinone staring material prepared as in Example 7 of WO 94/13652.

g) 5-Hydroxy-3-(3-trifluoromethylphenyl) oxazolidin-4-one

NMR δ: 4.20 (1H,brs), 5.50 (1H,d), 5.63–5.70 (2H,m), 7.45–7.58 (2H,m), 7.75–7.82 (2H,m).

Thiazolidinone starting material prepared as in Example 2 of WO 94/13652.

EXAMPLE 5

Conversion of a Compound of Formula I into a Compound of Formula III 5-t-Butylcarbamoyloxy-3-(3-trifluoromethylphenol)oxazolidin-4-one t-Butylisocyanate (1.77 g) was added to a sired solution of the compound of Example 4g) (4.41 g) in dichloromethane (20 ml). Triethylamine (1.81 g) was then added dropwise over 25 min. The resulting brown solution was stirred at room temperature for 2½ hours then left to stand overnight. The solvent was evaporated under reduced pressure to give a brown solid which was purified by flash chromatography using ethyl acetate/hexane 2:8 as elutant. The resulting solid was triturated with hexane to give the title compound as a white solid (3.49 g), mp. 122.4–123.8° C.

NMR δ: 1.35 (2H,m), 4.88 (1H,brs), 5.53 (1H,d), 5.65 (1H,m), 6.20 (1H,s), 7.52 (2H,m), 7.80 (2H,m).

We claim:

1. A process for the production of a hydroxyoxazolidinone of formula I:

I wherein A is phenyl optionally substituted by one or more substituents selected from halogen, $C_1$–$C_{10}$ hydrocarbyl, $S(O)_p$($C_1$–$C_{10}$ hydrocarbyl), cyano, nitro, SCN, $SiR^c_3$ (where each $R^c$ is independently $C_1$–$C_4$ alkyl or phenyl), $COR^{12}$, $CR^{12}NOR^{13}$, $ONR^{12}R^{13}$, $SF_5$, $COOR^{12}$, $SO_2NR^{12}R^{13}$, $OR^{14}$ or $NR^{15}R^{16}$;

alternatively, two substituents may combine to form a fused 5- or 6-membered saturated or partially saturated carbocyclic or heterocyclic ring in which any carbon or quaternised nitrogen atom may be substituted with any of the groups mentioned as substituents on A, a ring carbon atom may form part of a carbonyl group or a nitrogen atom may be oxidised;

p is 0, 1 or 2;

$R^{12}$ and $R^{13}$ independently represent hydrogen or $C_1$–$C_{10}$ hydrocarbyl;

$R^{14}$ is hydrogen, $C_1$–$C_{10}$ hydrocarbyl, $SO_2$($C_1$–$C_{10}$ hydrocarbyl), CHO, CO($C_1$–$C_{10}$ hydrocarbyl), COO ($C_1$–$C_{10}$ hydrocarbyl) or $CONR^{12}R^{13}$;

$R^{15}$ and $R^{16}$ independently represent hydrogen, $C_1$–$C_{10}$ hydrocarbyl, O($C_1$–$C_{10}$ hydrocarbyl), $SO_2$($C_1$–$C_{10}$ hydrocarbyl), CHO, CO($C_1$–$C_{10}$ hydrocarbyl), COO ($C_1$–$C_{10}$ hydrocarbyl) or $CONR^{12}R^3$; and any of the foregoing hydrocarbyl groups, whether the hydrocarbyl group is a group on its own or part of a larger group, may optionally be substituted with halogen, hydroxy, $SO_2NR^aR^b$ (where $R^a$ and $R^b$ independently represent hydrogen or $C_1$–$C_6$ alkyl), cyano, nitro, amino, mono- or di-$C_1$–$C_6$ alkylamino, acylamino, $C_1$–$C_6$ alkoxy, $C_1$–$C_6$ haloalkoxy, $C_1$–$C_6$ alkylthio, $C_1$–$C_6$ alkylsulfinyl, $C_1$–$C_6$ alkylsulfonyl, carboxy, carboxyamide (in which the groups attached to the N atom may be hydrogen or $C_1$–$C_{10}$ hydrocarbyl optionally substituted with halogen), $C_1$–$C_6$ alkoxycarbonyl or aryl;

which process comprises the step of treating a hydroxythiazolidinone of formula II:

II in which A is as defined for formula I; with an oxidising agent.

2. A process according to claim 1, wherein the oxidising agent comprises a periodate salt and a catalytic amount of a ruthenium salt.

3. A process according to claim 2, wherein the oxidising agent is sodium periodate.

4. A process according to claim 2, wherein the ruthenium salt is a halide.

5. A process according to claim 4, wherein the ruthenium salt is ruthenium trichloride.

6. A process according to claim 1, which is performed in a solvent comprising a mixture of water and a water-miscible organic solvent.

7. A process according to claim 6, wherein the water-miscible organic solvent is methanol or ethanol.

8. A process according to claim 1, wherein A represents phenyl optionally substituted with one or more substituents selected from halogen, $C_1$–$C_{10}$ hydrocarbyl and O($C_1$–$C_{10}$ hydrocarbyl).

9. A process according to claim 8, wherein A represents phenyl substituted with one or more substituents selected from halogen, $C_1$–$C_4$ alkyl, $C_1$–$C_4$ haloalkyl, O($C_1$–$C_4$ alkyl) and O($C_1$–$C_4$ haloalkyl).

10. A process for the production of a compound of formula III:

III wherein A is as defined for formula I in claim 1;

Z is O, S or $NR^4$;

W is O or S;

$R^1$ is hydrogen, or $C_1$–$C_{10}$ hydrocarbyl or heterocyclyl having 3 to 8 ring atoms either of which may optionally be substituted with halogen, hydroxy, $SO_2$ $NR^aR^b$ (where $R^a$ and $R^b$ independently represent hydrogen or $C_1$–$C_6$ alkyl), $SiR^c_3$ (where each $R^c$ is independently $C_1$–$C_4$ alkyl or phenyl), cyano, nitro, amino, mono- and di-$C_1$–$C_6$ alkylamino, acylamino, $C_1$–$C_6$ alkoxy, $C_1$–$C_6$ haloalkoxy, $C_1$–$C_6$ alkylthio, $C_1$–$C_6$ alkylsulfinyl $C_1$–$C_6$ alkylsulfonyl, carboxy, carboxyamide (in which the groups attached to the N atom may be hydrogen or optionally substituted $C_1$–$C_{10}$ hydrocarbyl), $C_1$–$C_6$ alkoxycarbonyl or aryl;

$R^4$ represents hydrogen or $C_1$–$C_4$ alkyl;

n is 0 or 1;

Y is O, S or $NR^5$;

$R^5$ is hydrogen, hydroxy, CHO or $NR^6R^7$, or $C_1$–$C_{10}$ hydrocarbyl or O($C_1$–$C_{10}$ hydrocarbyl) either of which may be substituted with up to two substituents selected from $OR^6$, $COR^6$, $COOR^6$, $OCOR^6$, cyano, halogen, $S(O)_pR^6$, $NR^6R^7$, nitro, $NR^6COR^7$, $NR^6CONR^7R^8$, $CONR^6R^7$ and heterocyclyl;

$R^6$, $R^7$ and $R^8$ independently represent hydrogen or $C_1$–$C_6$ hydrocarbyl optionally substituted by one or more halogen atoms;

p is 0, 1 or 2;

alternatively, when Y is $NR^5$ and either Z is $NR^4$ or n is 0, $R^5$ and $R^4$ or $R^1$ may together form a bridge represented by the formula —$Q^1$—$Q^2$— or —$Q^1$—$Q^2$—$Q^3$—, where $Q^1$, $Q^2$ and $Q^3$ independently represent $CR^9R^{10}$, =$CR^9$, CO, $NR^{11}$, =N, O or S;

$R^9$ and $R^{10}$ independently represent hydrogen, $C_1$–$C_4$ alkyl, hydroxy or halogen; and $R^{11}$ represents hydrogen or $C_1$–$C_4$ alkyl;

the process comprising producing a compound of formula I by a process according to claim 1 and converting it to a compound of formula III.

* * * * *